United States Patent [19]

Iwamatsu et al.

[11] Patent Number: 4,971,961
[45] Date of Patent: Nov. 20, 1990

[54] CEPHALOSPORIN COMPOUNDS AND ANTIBACTERIAL AGENTS

[75] Inventors: Kaysuyoshi Iwamatsu; Kenji Sakagami; Kunio Atsumi; Takashi Yoshida; Seiji Shibahara; Takashi Tsuruoka; Shinichi Kondo, all of Yokohama, Japan

[73] Assignee: Meiji Seika Kaisha, Ltd., Tokyo, Japan

[21] Appl. No.: 266,050

[22] Filed: Nov. 2, 1988

[30] Foreign Application Priority Data

Nov. 11, 1987 [JP] Japan ................. 62-284634

[51] Int. Cl.$^5$ ............. C07D 501/20; A61K 31/545
[52] U.S. Cl. ..................... 514/202; 540/222; 540/225; 540/226; 540/227; 540/230; 514/206; 514/207; 514/209
[58] Field of Search ............. 540/222, 225, 227, 230, 540/226; 514/206, 202, 209, 207

[56] References Cited

U.S. PATENT DOCUMENTS 4,822,786 4/1989 Zama et al. ............... 540/225

Primary Examiner—Nicholas S. Rizzo
Attorney, Agent, or Firm—Jordan and Hamburg

[57] ABSTRACT

This invention provides cephalosporin compounds represented by the following general formula:

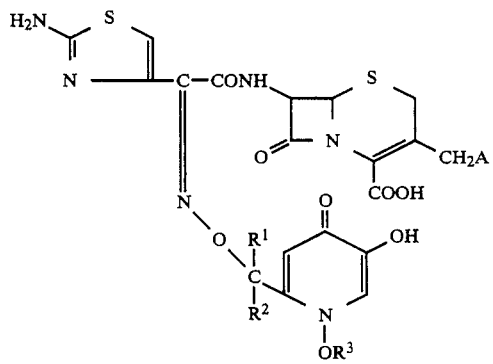

wherein $R^1$ and $R^2$ are same or different hydrogen atom or a lower alkyl group of 1 to 5 carbon atoms; $R^3$ is a lower alkyl group which may optionally be substituted with a halogen atome (or atoms), an alkenyl group, or a cycloalkylmethyl group of 3 to 6 carbon atoms; and A is hydrogen atom or residue of a nucleophilic compound and pharmacologically acceptable salts thereof. These compounds have broad-spectrum antibacterial activity against Gram-positive and -negative bacteria including *Pseudomonas aeruginosa*, as well as against a great variety of β-lactamase-producing strains.

12 Claims, No Drawings

CEPHALOSPORIN COMPOUNDS AND ANTIBACTERIAL AGENTS

BACKGROUND OF THE INVENTION

1. Field of the Invention

This invention relates to new cephalosporin derivatives having broad-spectrum antibacterial activity against bacteria including *Pseudomonas aeruginosa*. More particularly, it relates to new cephalosporin derivatives carrying, at the 7-position, a (Z)-2-(2-aminothiazol-4-yl)-2-(1-substituted-oxy-5-hydroxy -4-pyridon-2-yl)alkoxyiminoacetamido group, which have high therapeutical effects upon human and animal diseases caused by pathogenic bacteria.

2. Description of Prior Art

Cephalosporin antibiotics have been widely used for the therapy of diseases caused by pathogenic bacteria, but are not completely satisfactory in terms of antibacterial activity, antibacterial spectrum and therapeutical effects in clinical use.

We formerly found that new cephalosporin derivatives carrying, at the 7-position, a 2-(2- aminothiazol-4-yl)-2-(1,5-dihydroxy-4-pyridon-2-yl)alkoxyiminoacetamide group have high activity against a wide range of pathogenic bacteria (Japanese Patent Application No. 62-108229). These compounds showed particularly high antibacterial activity against Pseudomonas aeruginosa.

SUMMARY OF THE INVENTION

Noting the 1,5-dihydroxy-4-pyridone structure involved, we further expanded our studies on this type of compounds. As a result, it has been found that the new cephalosporin compounds represented by the formula (I) shown below have broad-spectrum antibacterial activity against Gram-positive bacteria and Gramnegative bacteria including Pseudomonas aeruginosa, and also against a great variety of β-lactamase-producing strains.

Thus, this invention relates to new cephalosporin compounds represented by the following general formula (I):

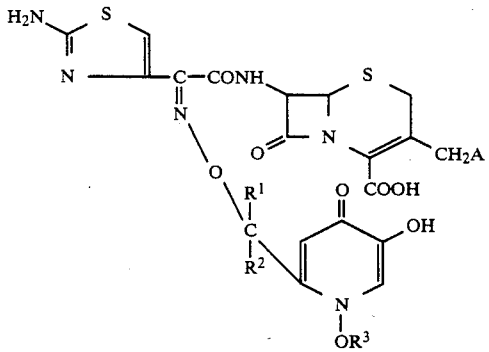

[wherein $R^1$ and $R^2$ are same or different hydrogen atom or a lower alkyl group of 1 to 5 carbon atoms; $R^3$ is a lower alkyl group which may optionally be substituted with a halogen atom (or atoms), an alkenyl group, or a cycloalkylmethyl group of 3 to 6 carbon atoms; and A is hydrogen atom or residue of a nucleophilic compound] and pharmacologically acceptable salts thereof, and to antibacterial agents containing the same as active ingredient.

The compounds of formula (I), when an asymmetric carbon atom is contained in the side chain at 7-position, can exist as D-and L-isomers. This invention includes both of these, as well as DL-isomers.

DETAILED DESCRIPTION OF THE INVENTION

As the pharmacologically acceptable salts of the compounds of formula (I) of this invention, may be mentioned medically acceptable salts (especially, commonly used nontoxic salts). These include salts of alkali metals (e.g., sodium and potassium); salts of alkaline earth metals (e.g., calcium and magnesium); ammonium salts; salts with organic bases (e.g., triethylamine, pyridine, ethanolamine, triethanolamine and dicyclohexylamine), and salts with basic amino acids (e.g., lysine and arginine).

As examples of substituent group $R^3$ in the compounds of general formula (I), there may be mentioned linear or branched alkyl groups (e.g., methyl, ethyl, propyl, isopropyl, n-butyl, isobutyl and t-butyl); halogenated alkyl groups (e.g., difluoromethyl, trifluoromethyl and 2-fluoroethyl); alkenyl groups (e.g., vinyl and allyl); and cycloalkylmethyl groups (e.g., cyclopropylmethyl and cyclopentylmethyl).

As the residue of nucleophilic compound A in the general formula (I) may be mentioned hydroxyl, mercapto, carbamoyl, carbamoyloxy, azido, alkanoyloxy groups of 2 to 5 carbon atoms, substituted and unsubstituted pyridinium radicals represented by the following general formula,

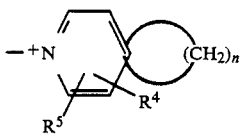

(wherein n is 0 or an integer of 3 to 5; and $R^4$ and $R^5$ are same or different hydrogen atom, a halogen atom, a linear or branched alkyl group of 1 to 5 carbon atoms, hydroxyl, amino, carbamoyl, sulfonic, sulfonamido, a sulfoalkyl, a linear or branched alkylthio group of 1 to 5 carbon atoms, a halogenated alkylthio group, a cycloalkylthio group, a cycloalkylmethylthio group, a carboxyalkylthio group, an alkoxyalkylthio group, or an alkyl-substituted-aminoalkylthio group), quaternary ammonium radicals such as quinolinium, isoquinolinium, thiazolinium and N-alkylpyrrolidinium radicals which may optionally have substituent groups, and heterocyclicthio groups.

The heterocyclic ring herein means a 5- or 6-membered ring containing 1 to 4 hetero atoms selected from O, S and N (e.g., pyridine, pyridine N-oxide, pyrimidine, pyridazine, pyridazine N-oxide, pyrazole, thiazole, thiadiazole, oxadiazole, triazole, tetrazole and triazine), or a bicyclic ring (e.g., cycloalkenopyridine, benzothiazole, benzimidazole, benzoxazole and triazaindole). These heterocyclic rings may optionally have substituent groups, such as lower alkyl of 1 to 3 carbon atoms, halogenated alkyl group, alkoxy, halogen, hydroxyl, mercapto, amino, carboxyl, carbamoyl, dialkylaminoalkyl, carboxymethyl, hydroxyalkyl and sulfoalkyl.

Group A may also be a substituted or unsubstituted pyridiniumthio radical represented by the following general formula:

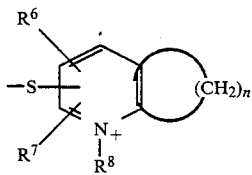

[wherein n is 0 or an integer of 3 to 5; $R^6$ and $R^7$ are same or different hydrogen atom, a halogen atom, or a lower alkyl group of 1 to 5 carbon atoms which may optionally contain a halogen atom (or atoms); $R^8$ is a linear or branched alkyl of 1 to 5 carbon atoms, a halogenated alkyl, cyclopropyl, cyclopropylmethyl, an alkenyl, oxygen atom, or a radical represented by—$(CH_2)mB$ in which m is 0 or an integer of 1 to 3; and B is hydroxyl, an alkoxyl, amino, an alkyl-substituted amino, carboxyl, carbamoyl, sulfonic, sulfonamido, hydroxamic, cyano, mercapto, an alkylthio, methane-sulfonylaminocarbonyl or acetamidosulfonyl)].

As illustrative examples of the 3-position substituent group in the compounds of this invention (I), there may be mentioned, among others, the radicals listed below.

Pyridiniummethyl, 4-methylpyridiniummethyl,
2,3-dimethylpyridiniummethyl,
2,3-cyclopentenopyridiniummethyl,
2,3-cyclohexenopyridiniummethyl,
4-carbamoylpyridiniummethyl,
3-carbamoylpyridiniummethyl,
4-methylthiopyridiniummethyl,
3-methylthiopyridiniummethyl,
2-methylthiopyridiniummethyl,
4-ethylthiopyridiniummethyl,
4-allylthiopyridiniummethyl,
2-allylthiopyridiniummethyl,
4-cyclopropylmethylthiopyridiniummethyl,
3-cyclopropylmethylthiopyridiniummethyl,
4-cyclopropylthiopyridiniummethyl,
4-cyclopentylthiopyridiniummethyl,
4-(2,2,2-trifluoroethyl)thiopyridiniummethyl,
4-(2-hydroxyethyl)thiopyridiniummethyl,
3-(2-hydroxyethyl)thiopyridiniummethyl,
2-(2-hydroxyethyl)thiopyridiniummethyl,
2-cyclopropylthiopyridiniummethyl,
4-trimethylsilylpyridiniummethyl,
3-trimethylsilylpyridiniummethyl,
4-trifluoromethylthiopyridiniummethyl,
4-(2-fluoroethyl)thiopyridiniummethyl,
4-carboxymethylthiopyridiniummethyl,
4-carbamoylmethylthiopyridiniummethyl,
4-(N,N-dimethylaminoethyl)thiopyridiniummethyl,
2,3-cyclopenteno-4-methylthiopyridiniummethyl,
2,3-cyclopenteno-4-ethylthiopyridiniummethyl,
2,3-cyclopenteno-4-allylthiopyridiniummethyl,
2,3-cyclopenteno-4-cyclopropylmethylthiopyridiniummethyl,
2,3-cyclopenteno-4-cyclopropylthiopyridiniummethyl,
2,3-cyclopenteno-4-pentylthiopyridiniummethyl,
2,3-cyclopenteno-4-(2,2,2-trifluoroethyl)thiopyridiniummethyl,
2,3-cyclopenteno-4-(2-hydroxyethyl)thiopyridiniummethyl,
2,3-cyclopenteno-4-(2-fluoroethyl)thiopyridiniummethyl,
2,3-cyclopenteno-4-carboxymethylthiopyridiniummethyl,
2,3-cyclopenteno-4-carbamoylmethylthiopyridiniummethyl,
2,3-cyclopenteno-4-(N,N-dimethylaminoethyl)thiopyridiniummethyl,
2,3-cyclohexeno-4-methylthiopyridiniummethyl,
2,3-cyclohexeno-4-cyclopropylmethylthiopyridiniummethyl,
2,3-cyclohexeno-4-cyclopropylthiopyridiniummethyl,
2,3-cyclohexeno-4-(2-hydroxyethyl)thiopyridiniummethyl,
2,3-cyclohexeno-4-(2,2,2-trifluoroethyl)thiopyridiniummethyl, 2,3-cyclohexeno-4-carboxylmethylthiopyridiniummethyl, 2,3-cyclohexeno-4-carbamoylmethylthiopyridiniummethyl, 5,6-cyclopenteno-2-methylthiopyridiniummethyl, 5,6-cyclopenteno-2-allylthiopyridiniummethyl, 5,6-cyclopenteno-2-cyclopropylthiopyridiniummethyl, 5,6-cyclopenteno-2-(2-hydroxyethyl)thiopyridiniummethyl, 5,6-cyclopenteno-2-(2-fluoroethyl)thiopyridiniummethyl, 5,6-cyclopenteno-2-carboxymethylthiopyridiniummethyl, 5,6-cyclopenteno-2-carbamoylmethylthiopyridiniummethyl, (quinolinium-1-yl)methyl, (3-aminoquinolinium-1-yl)methyl, (5-aminoquinolinium-1-yl)methyl, (5-hydroxyquinolinium-1-yl)methyl, (6-hydroxyquinolinium-1-yl)methyl, (7-hydroxyquinolinium-1-yl)methyl, (4-carbamoylquinolinium-1-yl)methyl, (5-trifluoromethylquinolinium-1-yl)methyl, (isoquinolinium-2-yl)methyl, (5-hydroxyisoquinolinium-2-yl)methyl, (4-hydroxyisoquinolinium-2-yl)methyl, (5-aminoisoquinolinium-2-yl)methyl, (4-aminoisoquinolinium-2-yl)methyl, (3-methylisoquinolinium-2-yl)methyl, (5-hydroxyisoquinolinium-2-yl)methyl, (8-hydroxyisoquinolinium-2-yl)methyl, (4-carbamoylisoquinolinium-2-yl)methyl, (5-trifluoromethylisoquinolinium-2-yl)methyl, (thieno[3,2-c]pyridinium-5-yl)methyl, (thieno[2,3-b]pyridinium-7-yl)methyl,
(thieno[3,2-b]pyridinium-4-yl)methyl,
(thieno[2,3-c]pyridinium-6-yl)methyl,
(thieno[3,4-b]pyridinium-4-yl)methyl,
(thieno[3,4-c]pyridinium-5-yl)methyl,
(4-methylthieno[2,3-b]pyridinium-7-yl)methyl,
(furo[2,3-c]pyridinium-6-yl)methyl,
(furo[3,2-c]pyridinium-5-yl)methyl,
(furo[2,3-b]pyridinium-7-yl)methyl,
(furo[3,2-b]pyridinium-4-yl)methyl,
(2-methylfuro[3,2-b]pyridinium-4-yl)methyl,
(2,4-dimethylfuro[2,3-b]pyridinium-4-yl)methyl,
(thiazol[4,5-c]pyridinium-5-yl)methyl,
(2-aminothiazolo[4,5-c]pyridinium-5-yl)methyl,
(2-methylthiazolo[4,5-c]pyridinium-5-yl)methyl,
(1,3-dihydrofuro[3,4-b]pyridinium-4-yl)methyl,
(1,3-dihydropyrrolo[3,4-b]pyridinium-4-yl)methyl,
(2 methyl-1,3-dihydropyrrolo[3,4-b]pyridinium-4-yl)methyl, (2,2-dimethyl-1,3-dihydropyrrolo[3,4-b]pyridinium-4-yl)methyl, (1,3-dihydrothieno[3,4-b]pyridinium-4-yl)methyl, (2-oxo-1,3-dihydrothieno[3,4-b]pyridinium-4-yl)methyl, (pyrazinium-1-yl)methyl,
(3-methylpyrazinium-1-yl)methyl,
(3,5-dimethylpyrazinium-1-yl)methyl,
[3-(2-hydroxyethyl)aminopyrazinium-1-yl)methyl,
(3-aminopyrazinium-1-yl)methyl,
(3-dimethylaminopyrazinium-1-yl)methyl, (thiazolinium-3-yl)methyl, (4-methylthiazolinium-3-yl)methyl, (1-methylpyrrolidinium-1-yl)methyl, trimethylammoniummethyl,
N,N-dimethyl-N-(2-hydroxyethyl)ammoniummethyl,
N,N-dimethyl-N-allylammoniummethyl,
N,N-diethyl-N-methylammoniummethyl,
(1H-tetrazol-5-yl)thiomethyl,
(1-methyl-1H-tetrazol-5-yl)thiomethyl,
(1-amino-1H-tetrazol-5-yl)thiomethyl,
[1-(2-dimethylaminoethyl)-1H-tetrazol-5-yl]thiomethyl,
[1-(2-hydroxyethyl)-1H-tetrazol-5-yl]thiomethyl,
[1-(2-carboxyethyl)-1H-tetrazol-5-yl]thiomethyl,
(1-carboxymethyl-1H-tetrazol-5-yl)thiomethyl,
(1-carbamoylmethyl-1H-tetrazol-5-yl)thiomethyl,
(1-sulfomethyl-1H-tetrazol-5-yl)thiomethyl,
[1-(2-sulfoethyl)-1H-tetrazol-5-yl]thiomethyl,
(1-sulfamoylmethyl-1H-tetrazol-5-yl)thiomethyl,
(1,3,4-thiadiazol-5-yl)thiomethyl,
(2-methyl-1,3,4-thiadiazol-5-yl)thiomethyl,
(2-trifluoromethyl-1,3,4-thiadiazol-5-yl)thiomethyl,
(2-carboxy-1,3,4-thiadiazol-5-yl)thiomethyl,
(2-methylamino-1,3,4-thiadiazol-5-yl)thiomethyl,
(2-carbamoyl-1,3,4-thiadiazol-5-yl)thiomethyl,
(2-ethoxycarbonyl-1,3,4-thiadiazol-5-yl)thiomethyl,
(2-amino-1,3,4-thiadiazol-5-yl)thiomethyl,
(2-mercapto-1,3,4-thiadiazol-5-yl)thiomethyl,
(2-carbamoylmethyl-1,3,4-thiadiazol-5-yl)thiomethyl,
(1,2,3-thiadiazol-5-yl)thiomethyl,
(4-methyl-1,2,3-thiadiazol-5-yl)thiomethyl,
(4-carbamoyl-1,2,3-thiadiazol-5-yl)thiomethyl,
(4-ethoxycarbonyl-1,2,3-thiadiazol-5-yl)thiomethyl,
(4-carboxy-1,2,4-thiadiazol-5-yl)thiomethyl,
(1,2,4-thiadiazol-5-yl)thiomethyl,
(3-methyl-1,2,4-thiadiazol-5-yl)thiomethyl,
(3-phenyl-1,2,4-thiadiazol-5-yl)thiomethyl,
(thiazol-2-yl)thiomethyl, (4-methylthiazol-2-yl)thiomethyl,
(4-phenylthiazol-2-yl)thiomethyl,
(4-trifluoromethylthiazol-2-yl)thiomethyl,
(4-carboxymethylthiazol-2-yl)thiomethyl,
(5-methylthiazol-2-yl)thiomethyl, (5-phenylthiazol-2-yl)thiomethyl, (thiazol-5-yl)thiomethyl,
(4-carbamoylthiazol-5-yl)thiomethyl,
(4-carboxy-3-hydroxyisothiazol-5-yl)thiomethyl,
(4-cyano-3-hydroxyisothiazol-5-yl)thiomethyl,
(1,3,4-oxadiazol-5-yl)thiomethyl,
(2-methyl-1,3,4-oxadiazol-5-yl)thiomethyl,
(2-phenyl-1,3,4-oxadiazol-5-yl)thiomethyl,
(2-carboxymethyl-1,3,4-oxadiazol-5-yl)thiomethyl,
(1,2,4-oxadiazol-5-yl)thiomethyl,
(3-methyl-1,2,4-oxadiazol-5-yl)thiomethyl,
(3-phenyl-1,3,4-oxadiazol-5-yl)thiomethyl,
(oxazol-2-yl)thiomethyl, (4-methyloxazol-2-yl)thiomethyl, (pyrazol-5-yl)thiomethyl,
(1-methylimidazol-2-yl)thiomethyl,
(1H-1,2,3-triazol-5-yl)thiomethyl,
(1-methyl-1H-1,2,3-triazol-5-yl)thiomethyl,
(1H-1,2,4-triazol-5-yl)thiomethyl,
(1-methyl-1H-1,2,4-triazol-5-yl)thiomethyl, (4-methyl-3-trifluoromethyl-4H-1,2,4-triazol-5-yl)thiomethyl,
(1H-1,3,4-triazol-5-yl)thiomethyl,
(1-methyl-1H-1,3,4-triazol-5-yl)thiomethyl,
(1-carboxymethyl-1H-1,3,4-triazol-5-yl)thiomethyl,
(1-carbamoylmethyl-1H-1,3,4-triazol-5-yl)thiomethyl,
(2-methyl-1H-1,3,4-triazol-5-yl)thiomethyl,
(2-carboxymethyl-1H-1,3,4-triazol-5-yl)thiomethyl,
(2-phenyl-1H-1,3,4-triazol-5-yl)thiomethyl,
(2,5-dihydro-2-methyl-5-oxo-6-hydroxy-1,2,4-triazin-3-yl)thiomethyl,
(4,5-dihydro-4-methyl-5-oxo-6-hydroxy-1,2,4-triazin-3-yl)thiomethyl,
(2,3-dihydro-3-methyl-2-oxo-6-hydroxy-1,3,5-triazin-4-yl)thiomethyl,
(3,4-dihydro-4-methyl-1,1,3-trioxo-2H-1,2,4,6-thiatriazin-5-yl)thiomethyl,
(5-methyl-s-triazolo[1,5-a]pyrimidin-7-yl)thiomethyl,
(2-carboxy-5-methyl-s-triazolo[1,5-a]pyrimidin-7-yl)thiomethyl, (pyridazin-3-yl)thiomethyl,
(N-oxypyridazin-3-yl)thiomethyl,
(pyrimidin-2-yl)thiomethyl, (benzothiazol-2-yl)thiomethyl, (benzimidazol-2-yl)thiomethyl,
(benzoxazol-2-yl)thiomethyl, (3H-4-quinazolin-2-yl)thiomethyl, (pyridin-4-yl)thiomethyl, (pyridin-3-yl)thiomethyl, (pyridin-2-yl)thiomethyl,
(3-methylpyridin-4-yl)thiomethyl, (2,3-dimethylpyridin-4-yl)thiomethyl,
(2-carboxypyridin-4-yl)thiomethyl,
(2-carbamoylpyridin-4-yl)thiomethyl,
(2,3-cyclopentenopyridin-4-yl)thiomethyl,
(pyridine-N-oxid-4-yl)thiomethyl,
(5,6-cyclopentenopyridin-2-yl)thiomethyl,
(2,3-cyclohexenopyridin-4-yl)thiomethyl,
(5,6-cyclohexenopyridin-2-yl)thiomethyl,
(1-methylpyridinium-4-yl)thiomethyl,
(1-methylpyridinium-2-yl)thiomethyl,
(1-methylpyridinium-3-yl)thiomethyl,
(1-ethylpyridinium-4-yl)thiomethyl,
(1-allylpyridinium-4-yl)thiomethyl,
[1-(2,2,2-trifluoroethyl)pyridinium-4-yl]thiomethyl,
(1-carboxymethylpyridinium-4-yl)thiomethyl,
(1-carbamoylmethylpyridinium-4-yl)thiomethyl,
[1-(1-carboxyethyl)pyridinium-4-yl]thiomethyl,
[1-(2-hydroxyethyl)pyridinium-4-yl]thiomethyl,
[1-2-(dimethylaminoethyl)pyridinium-4-yl]thiomethyl,
(1-cyclopropylpyridinium-4-yl)thiomethyl,
(1-cyclopropylmethylpyridinium-4-yl)thiomethyl,
(1-methylthiomethylpyridinium-4-yl)thiomethyl,
(1-cyanomethylpyridinium-4-yl)thiomethyl,
[1-(2-fluoroethyl)pyridinium-4-yl]thiomethyl,
(1-hydroxyaminocarbonylmethylpyridinium-4-yl)thiomethyl,
[1-(2-sulfoethyl)-pyridinium-4-yl]thiomethyl,
(1-sulfomethylpyridinium-4-yl)thiomethyl,
(1-sulfamoylmethylpyridinium-4-yl)thiomethyl, (1-N,N-dimethylsulfamoylmethylpyridinium-4-yl)thiomethyl,
(2,6-dimethyl-1-carboxymethylpyridinium-4-yl)thiomethyl,
(3,5-dimethyl-1-carboxymethylpyridinium-4-yl)thiomethyl,
(2-carboxy-1-methylpyridinium-4-yl)thiomethyl,
(1-ethylpyridinium-3-yl)thiomethyl,
(1-allylpyridinium-3-yl)thiomethyl,
(1-cyclopropylpyridinium-3-yl)thiomethyl,
[1-(2-hydroxyethyl)pyridinium-3-yl]thiomethyl,
(1-carboxymethylpyridinium-3-yl)thiomethyl,
(1-carbamoylmethylpyridinium-3-yl)thiomethyl,
[1-(2-fluoroethyl)pyridinium-3-yl]thiomethyl,
[1-(2,2,2-trifluoroethyl)pyridinium-3-yl]thiomethyl,
(1-sulfomethylpyridinium-3-yl)thiomethyl,
(1-sulfamoylmethylpyridinium-3-yl)thiomethyl,
[1-(2-sulfoethyl)pyridinium-3-yl]thiomethyl,
(1-ethylpyridinium-2-yl)thiomethyl,
(1-allylpyridinium-2-yl)thiomethyl,
(1-cyclopropylpyridinium-2-yl)thiomethyl,

[1-(2-hydroxyethyl)pyridinium-2-yl]thiomethyl,
(1-carboxymethylpyridinium-2-yl)thiomethyl,
(1-carbamoylmethylpyridinium-2-yl)thiomethyl,
[1-(1-carboxyethyl)pyridinium-2-yl]thiomethyl,
[1-(2-fluoroethyl)pyridinium-2-yl]thiomethyl,
[1-(2,2,2-trifluoroethyl)pyridinium-2-yl]thiomethyl,
(1-sulfomethylpyridinium-2-yl)thiomethyl,
(1-sulfamoylmethylpyridinium-2-yl)thiomethyl,
[1-(2-sulfoethyl)pyridinium-2-yl]thiomethyl,
(2,3-cyclopenteno-1-methylpyridinium-4-yl)thiomethyl,
(2,3-cyclopenteno-1-ethylpyridinium-4-yl)thiomethyl,
(2,3-cyclopenteno-1-allylpyridinium-4-yl)thiomethyl,
[2,3-cyclopenteno-1-(2,2,2-trifluoroethyl)pyridinium-4-yl]thiomethyl, (2,3-cyclopenteno-1-carboxymethylpyridinium-4-yl)thiomethyl, (2,3-cyclopenteno-1-carbamoylmethylpyridinium-4-yl)thiomethyl, [2,3-cyclopenteno-1-(2-hydroxyethyl)pyridinium-4-yl]thiomethyl,
(2,3-cyclopenteno-1-dimethylaminoethylpyridinium-4-yl)thiomethyl, (2,3-cyclopenteno-1-cyclopropylpyridinium-4-yl)thiomethyl,
(2,3-cyclopenteno-1-cyclopropylmethylpyridinium-4-yl)thiomethyl,
(2,3-cyclopenteno-1-cyanomethylpyridinium-4-yl)thiomethyl,
(2,3-cyclopenteno-1-sulfomethylpyridinium-4-yl)thiomethyl, [2,3-cyclopenteno-1-(2-fluoroethyl)pyridinium-4-yl]thiomethyl, [2,3-cyclopenteno-1-(2-sulfoethyl)pyridinium-4-yl]thiomethyl,
[2,3-cyclopenteno-1-(2-sulfamoylethyl)pyridinium-4-yl]thiomethyl,
(5,6-cyclopenteno-1-methylpyridinium-2-yl)thiomethyl,
(5,6-cyclopenteno-1-ethylpyridinium-2-yl)thiomethyl,
(5,6-cyclopenteno-1-allylpyridinium-2-yl)thiomethyl,
[5,6-cyclopenteno-1-(2-fluoroethyl)pyridinium-2-yl]thiomethyl, [5,6-cyclopenteno-(2-hydroxyethyl)-pyridinium-2-yl]thiomethyl,
(5,6-cyclopenteno-1-carboxymethylpyridinium-2-yl)thiomethyl,
(2,3-cyclohexeno-1-methylpyridinium-4-yl)thiomethyl,
(2,3-cyclohexeno-1-carboxymethylpyridinium-4-yl)thiomethyl,
(2,3-cyclohexeno-1-carbamoylpyridinium-4-yl)thiomethyl, [2,3-cyclohexeno-1-(2-hydroxyethyl)-pyridinium-4-yl]thiomethyl,
[2,3-cyclohexeno-1-(dimethylaminoethylpyridinium-4-yl]thiomethyl, and (2,3-dihydro-1H-indolidinium-5-yl)thiomethyl.

The protected 2-hydroxymethyl-1-substituted-oxy-5-hydroxy-4-pyridone (IV), which is a component of the substituent at the 7-position, was prepared according to the method described below.

A protected kojic acid (II) was allowed to react with hydroxylamine hydrochloride in the presence of a base, such as pyridine, to form a compound (III), which was in turn allowed to react with a compound of $R^3X$ (in which $R^3$ is as defined above, and X is a halogen atom), as shown in the following equations:

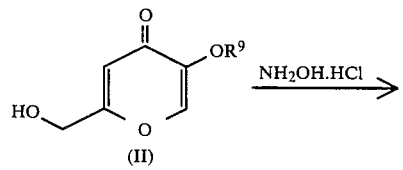

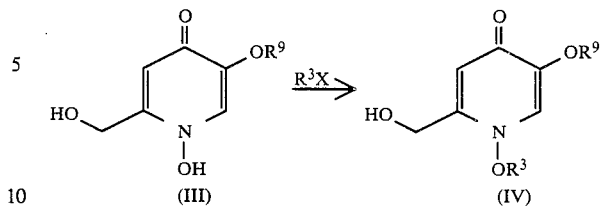

(wherein $R^9$ is a removable protective group, such as benzyl, p-nitrobenzyl, o-nitrobenzyl, p-methoxybenzyl and benzhydryl; and $R^3$ is as defined above.

The cephalosporin compounds of this invention represented by the general formula (I) can be synthesized by methods (A and (B) detailed below.

(A) Reaction of a compound represented by the following general formula (V):

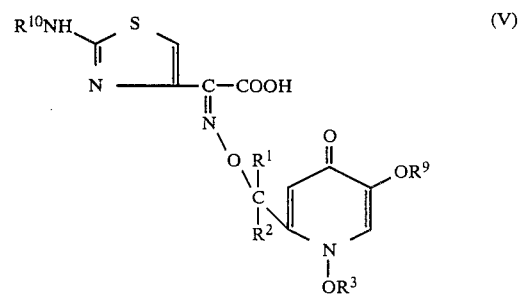

(wherein $R^{10}$ is hydrogen atom or a protective group for amine; and $R^1$, $R^2$, $R^3$ and $R^9$ are as defined above), or a carboxyl reactive derivative thereof, with a compound (VI) represented by the following general formula:

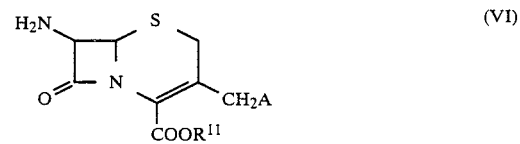

(wherein $R^{11}$ is hydrogen atom or a protective group for carboxyl; and A is as defined above) or a salt or a silyl derivative thereof, followed by removal of the protective groups.

(B) Reaction of a compound represented by the following general formula (VII):

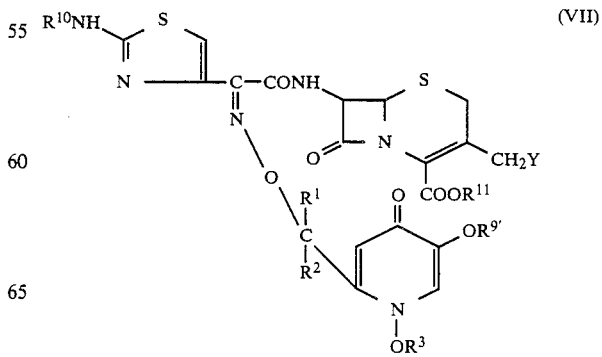

(wherein Y is acetoxy group or a halogen atom; $R^{9'}$ denotes hydrogen atom or $R^9$ group: and $R^1$, $R^2$, $R^3$, $R^9$, $R^{10}$ and $R^{11}$ are as defined above) with a nucleophilic compound, followed by removal of the protective groups as required, in which the nucleophilic compound is the one that corresponds to group A in the general formula (I).

As the protective groups for the amino and carboxyl groups in the above general formulas, may be adopted those which are commonly used in the field of β-lactam and peptide synthesis.

As examples of the protective groups for amino, there may be mentioned, among others, phthaloyl, formyl, monochloroacetyl, dichloroacetyl, trichloroacetyl, methoxycarbonyl, ethoxycarbonyl, t-butoxycarbonyl, trichloroethoxycarbonyl, benzyloxycarbonyl, p-nitrobenzyloxycarbonyl, diphenylmethyloxycarbonyl, methoxymethyloxycarbonyl, trityl and trimethylsilyl. On the other hand, as the protective groups for carboxyl, there may be mentioned, among others, t-butyl, t-amyl, allyl, benzyl, p-nitrobenzyl, p-methoxybenzyl, benzhydryl, phenyl, p-nitrophenyl, methoxymethyl, ethoxymethyl, benzyloxymethyl, acetoxymethyl, methylthiomethyl, trityl, trichloroethyl, trimethylsilyl and dimethylsilyl.

The condensation between compounds (V) and (VI) in the preparative method (A) is effected by the acylation method generally used for the synthesis of penicillin and cephalosporin compounds.

As the reactive derivatives, may be used acid halides, acid anhydrides, active amides and active esters. Preferred examples include acid chlorides; acid bromides; mixed acid anhydrides containing acetic, pivalic, isovaleric or trichloroacetic acid; active amides with pyrazole, imidazole, dimethylpyrazole and benzotriazole; and active esters with p-nitrophenol, 2,4-dinitrophenol, trichlorophenol, 1-hydroxy-1H-pyridone, N-hydroxysuccinimide, N-hydroxybenzotriazole and N-hydroxyphthalimide.

When a compound (V) is used in the form of free acid, the reaction is carried out preferably in the presence of a condensation agent. As examples of the condensation agent, may be mentioned carbodiimide compounds, such as N,N'-dicyclohexylcarbodiimide, N-cyclohexyl-N'-morpholinoethylcarbodiimide and N-cyclohexyl-N'-(4-diethylaminocyclohexyl)carbodiimide; and the so-called Vilsmeier reagents formed by the reaction of an amide compound ( e.g., N-methylformamide and N,N-dimethylformamide) with a halogenation reagent (e.g., thionyl chloride, phosphorus oxychloride and phosgen).

When an acid halide or an acid anhydride is used as the reactive derivative, the reaction must be carried out in the presence of base. As examples of the base, there may be mentioned organic bases, such as triethylamine, trimethylamine, ethyldiisopropylamine, N,N-dimethylamine, N-methylmorpholine and pyridine; or an inorganic base such as sodium hydrogen carbonate, sodium carbonate and potassium carbonate.

The reaction is normally carried out in a solvent having no adverse effect thereupon, such as water, acetone, acetonitrile, dioxane, tetrahydrofuran, ethyl acetate, dichloromethane, chloroform, dichloroethane, N,N-dimethylformamide, N,N-dimethylacetamide, dimethyl sulfoxide and mixtures thereof.

There is no specific limitation upon the reaction temperature, but the reaction is generally carried out at temperatures in the range of −30° to 40° C. and is put to completion in 0.5 to 10 hours.

The acylated compounds thus obtained may be freed from the protective groups by a proper method selected, depending on the type of group, from those commonly employed in the field of β-lactam and peptide synthesis (e.g., methods using an acid, a base or hydrazine).

The compounds of general formula (V) can be prepared by reaction of a compound represented by the following general formula (VIII):

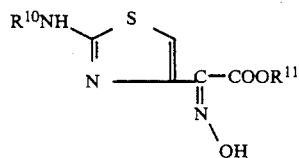

(wherein $R^{10}$ and $R^{11}$ are as defined above), or a salt thereof, with a compound represented by the following general formula (IX):

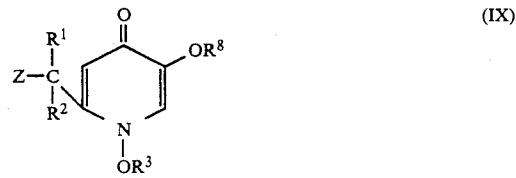

(wherein Z is a halogen atom, or a sulfonate group such as mesyloxy, tosyloxy and trifluoromesyloxy; $R^1$, $R^2$ and $R^3$ are as defined above), followed by removal of the protective groups as required.

This condensation reaction may be carried out in a solvent at temperatures in the range of −50° to 70° C. in the presence of a base as required. The solvent and base may be selected from those used in the acylation reaction described above.

The reaction of a compound (VII) with a nucleophilic compound in the preparative method (D) is carried out by a method commonly employed for cephalosporin synthesis. When group Y in the general formula (VII) is acetoxy, the reaction is preferably carried out in water, a phosphate buffer, a polar solvent (e.g., acetone, acetonitrile, N,N-dimethyl formamide, N,N-dimethylacetamide, tetrahydrofuran, dimethyl sulfoxide, dioxane, methanol and ethanol), or a mixture thereof with water.

The reaction is allowed to proceed preferably at temperatures from room temperature to about 80° C. under near neutral conditions. The reaction time may vary with the other reaction conditions but is usually in the range from 1 to 10 hours.

This reaction can be accelerated by the addition of an alkali metal halide, such as sodium iodide and potassium iodide.

When group Y in the general formula (VII) is a halogen atom, on the other hand, the reaction is preferably carried out in a solvent (e.g., acetone, dioxane, tetrahydrofuran, ethyl acetate, acetonitrile, N,N-dimethylformamide, N,N-dimethylacetamide and dimethyl sulfoxide) under anhydrous conditions at temperatures in the range of 0° to 50° C. The reaction is usually complete in 1 to 5 hours.

The compounds (I) thus formed can be isolated from the reaction mixture by usual methods, for example, by a proper combination of treatment with an adsorptive resin [e.g., Amberlite XAD-2 (Rohm & Haas) and Diaion HP-20 (Mitsubishi Chemical Industries, Ltd.)], precipitation, crystallization and other purification techniques.

The antibacterial agents containing, as main ingredient, a compound represented by the general formula (I) or a salt thereof are used in various dosage forms, such as parenteral injections (e.g., intravenous and muscular injections); oral agents (e.g., capsules, tablets and powder); rectal agents; greasy suppositories; and water-soluble suppositories. These pharmaceutical preparations can be made by usual methods by the use of commonly employed additives, such as excipients, fillers, binders, humectants, disintegrators, surface-active agents, lubricants, dispersants, buffering agents, preservatives, solubilizers, antiseptics, flavoring agents and analgesics.

The suitable daily dose should be properly set case by case considering the conditions, age, sex and other factors of patient, but is generally in the range of 250 to 3000 mg, which is subdivided in 1 to 4 doses.

The compounds of this invention represented by the general formula (I) and salts thereof are novel compounds and show high antibacterial activity against the growth of a wide range of pathogenic bacteria including Gram-positive and -negative bacteria.

To illustrate the utility of the compounds (I) of this invention, the antibacterial activity of some of these compounds is summarized in Table 1.

TABLE 1

| Minimum Growth Inhibition Concentration (μg/ml) | | | | | |
| --- | --- | --- | --- | --- | --- |
| | | Exp. 1 | Exp. 2 | Exp. 3 | Ceftazidime |
| Staphylococcus aureus | 209P JC-1 | 0.39 | 1.56 | 1.56 | 3.13 |
| Staphylococcus aureus | Smith (1) | 0.39 | 1.56 | 1.56 | 3.13 |
| Bacillus subtilis | ATCC 6633 | 0.78 | 1.56 | 1.56 | 6.25 |
| Escherichia coli | No. 29 | 0.10 | 0.05 | 0.05 | 0.20 |
| " | 255 | 3.13 | 0.39 | 0.78 | 12.5 |
| Klebsiella pneumoniae | GN-69 | 0.10 | 0.05 | 0.05 | 0.10 |
| Proteus vulgaris | GN-76 | 0.10 | 0.10 | 0.10 | 0.05 |
| Citobacter freundii | GN-346 | 6.25 | 6.25 | 12.5 | 50 |
| Enterobacter cloacae | GN-7471 | 6.25 | 1.56 | 1.56 | 3.13 |
| Serratia marcescens | No. 1 | 0.10 | 0.10 | 0.10 | <0.025 |
| Pseudomonas aeruginosa | M-0148 | 3.13 | 1.56 | 1.56 | 3.13 |
| Pseudomonas aeruginosa | E-2 | 0.78 | 0.20 | 0.20 | 1.56 |
| Pseudomonas aeruginosa | IAM-1007 | 1.56 | 0.10 | 0.10 | 1.56 |
| Pseudomonas sepacia | M-0527 | 0.05 | <0.025 | <0.025 | 0.78 |

The following examples will further illustrate the invention but are not intended to limit its scope. Needless to say, various changes and modifications may be made without departing from the spirit and scope of this invention.

The NMR data (values at 400 MHz) shown in the following examples are those when the value for water is taken as 4.82 in the case of heavy water, and those when TMS is used as internal standard in the case of the other deuterated solvents.

REFERENCE EXAMPLE 1

5-p-Methoxybenzyloxy-1-hydroxy-2-hydroxymethyl-4-pyridone (a) To a solution of 42.6 g kojic acid in 350ml N,N-dimethylformamide, were added 82.8 g anhydrous potassium carbonate and 55 g p-methoxybenzyl chloride, and the mixture was heated at 70°–75° C. for 1.5 hours. The reaction mixture was concentrated to about half its volume, and the concentrate was added to 700 ml water under ice cooling. The precipitate which separated out was collected by filtration, washed with water and ethyl acetate in that order, and dried, giving 59.9 g of 5-p-methoxybenzyloxy-2-hydroxymethyl-4-pyrone.

NMR (CDCl$_3$), δ:
3.80 (3H, s), 4.43 (2H, s), 4.96 (2H, s), 6.50 (1H, s), 6.88 (2H, d), 7.30 (2H, d), 7.51 (1H, s)

(b) To a solution of 39.3 g 5-p-methoxybenzyloxy-2-hydroxymethyl-4-pyrone in 600 ml pyridine, was added 52.2 g hydroxylamine hydrochloride, and the mixture was heated at 70°–75° C. for 2.5 hours. The reaction mixture was concentrated to about 100 ml, 100 ml water was added to the concentrate, and the resulting solution was added under ice cooling to a mixture of 75 ml hydrochloric acid and 225 ml water. After adjusting the pH to 2-2.5, stirring was continued under ice cooling for 30 minutes, and the crystals which separated out were collected by filtration, washed with water and dried, giving 16.6 g of 5-p-methoxybenzyloxy-1-hydroxy-2-hydroxymethyl-4-pyridone.

NMR (DMSO-d$_6$), δ:
3.76 (3H, s), 4.46 (2H, s), 5.03 (2H, s), 6.86 (1H, s), 6.93 (2H, d), 7.37 (2H, d), 7.97 (1H, s)

REFERENCE EXAMPLE 2

1-Methoxy-5-p-methoxybenzyloxy-2-hydroxymethyl-4-pyridone

Anhydrous potassium carbonate was dissolved in a suspension of 5.54 g 5-p-methoxybenzyloxy-1-hydroxy-2-hydroxymethyl-4-pyridone in 80 ml DMF, 1.5 ml methyl iodide was added, and the mixture was held at room temperature for one hour. The reaction mixture was concentrated under reduced pressure, 50 ml water was added to the residue, the resulting mixture was extracted twice with 100ml dichloromethane, and the extract was dried over anhydrous magnesium sulfate and concentrated.

Dichloromethane (25 ml) and ethyl acetate (50 ml) were added to the residue, and the crystals which separated out were collected by filtration and dried, giving 4.39 g of 1-methoxy-5-p-methoxybenzyloxy-2-hydroxymethyl-4-pyridone.

NMR (DMSO-d), δ:
3.77 (3H, s), 4.00 (3H, s), 4.45 (2H, bs), 4.92 (2H, s), 5.60 (1H, t), 6.13 (1H, s), 6.93 (2H, d), 7.35 (2H, d), 7.90 (1H, s)

REFERENCE EXAMPLE 3

1-Ethoxy-5-p-methoxybenzyloxy-2-hydroxymethyl-4-pyridone

This compound was prepared in much the same manner as in Reference Example 2, except that ethyl iodide was used in place of methyl iodide.

NMR (CDCl₃), δ:
1.27 (3H, t), 3.78(3H, s), 4.15 (2H, q), 4.57 (2H, s), 5.01 (2H, s), 6.60
1H, s), 6.83 (2H, d), 7.22 (1H, s),
7.29 (2H, d)

EXAMPLE 1

(6R,7R)-7-[(Z)-2-(2-aminothiazol-4-yl)-2-(1-methoxy-5-hydroxy-4-pyridon-2-yl)methoxyiminoacetamido]-3-(1,2,3-thiadiazol-5-yl)thiomethyl-ceph-3-em-4-carboxylic acid (a) To a suspension of 2.91 g 1-methoxy-5-p-methoxybenzyloxy-2-hydroxymethyl-4-pyridone in 70 ml dichloromethane, were added 0.1 ml N,N-dimethylformamide and 2.5 ml thionyl chloride at −15° C., and the mixture was held at that temperature for two hours.

Saturated aqueous solution of sodium bicarbonate (140 ml) and dichloromethane (70 ml) were added to the reaction mixture, and the organic layer was washed with water, dried over anhydrous magnesium sulfate and concentrated under reduced pressure. The residue was dissolved in 40 ml N,N-dimethylformamide, 4.22 g allyl (Z)-2-(tritylaminothiazol-4-yl)-2-hydroxyiminoacetate and 2.5 g anhydrous potassium carbonate were added, and the mixture was held at room temperature for 15 hours.

Chloroform (300 ml) was added to the reaction mixture, and the resulting mixture was washed with water, dilute hydrochloric acid and water in that order, dried over anhydrous magnesium sulfate, and concentrated under reduced pressure.

The residue was dissolved in 15 ml dichloromethane, 15 ml ethyl acetate and 30 ml isopropyl ether were added, and the crystals which separated out were collected by filtration, giving 5.7 g of allyl (Z)-2-(2-tritylaminothiazol-4-1)-2-(1-methoxy-5-p -methoxybenzyloxy-4-pyridon-2-yl)methoxyiminoacetate.

NMR (CDCl₃), δ:
3.80 (3H, s), 3.87 (3H, s), 4.77 (2H, d), 5.10 (2H, s), 5.15 (2H, s), 5.26 (1H, d), 5.38 (1H, d), 5.90 (1H, m), 6.46 (1H, s), 6.54 (1H, s), 6.88 (2H, d), 6.95 (1H, s), 7.13 (1H, s), 7.30 (17H, m)

(b) The allyl ester obtained in (a) above (5.57 g) was dissolved in 75 ml dichloromethane, 1.56 g sodium 2-ethyl hexanoate and 105 mg tetrakis (triphenylphosphine) palladium were added, and the mixture was held at room temperature for 1.5 hours. To the reaction mixture, were added 50 ml chloroform, 50 ml water and 15 ml 1N-HCl, and the organic layer was washed with water, dried over anhydrous magnesium sulfate and concentrated under reduced pressure. The residue was recrystallized from a mixture of dichloromethane and ethyl acetate, giving 4.48 g of (Z)-2-(2-tritylaminothiazol-4-yl)-2-(1-methoxy-5-p-methoxybenzyloxy-4-pyridon-2-yl)methoxyiminoacetic acid.

NMR (CDCl₃), δ:
3.74 (3H, s), 4.02 (3H, s), 4.98 (2H, s), 5.16 (2H, s), 6.64 (1H, s), 6.82 (2H, d ), 6.88 (1H, s), 7.30 (18H, m), 7.50 (1H, s)

(c) To a solution of 1.4 g of the acid obtained above in 40 ml dichloromethane, were added 1.08 g p-toluenesulfonic acid salt of p-methoxybenzyl (6R,7R)-7-amino-3-chloromethyl-ceph-3-em-4-carboxylate and 0.8 ml pyridine at −5° C. After a clear solution was obtained, 0.2 ml phosphorus oxychloride was added at −10° to −15° C., and the mixture was held at that temperature for 30 minutes. Dichloromethane (100ml) was added to the reaction mixture, and the resulting solution was washed twice with 50 ml of 15% aqueous solution of sodium chloride, dried over anhydrous magnesium sulfate and concentrated to dryness under reduced pressure, giving 2.4 of crude p-methoxybenzyl (6R,7R)-7-[(Z)-2-(2-tritylaminothiazol-4-yl)-2-(1-methoxy -5-p-methoxybenzyloxy-4-pyridon-2-yl)methoxyiminoacetamido]-3-chloromethyl-ceph-3-em-4-carboxylate as powder.

This crude product can be purified, as required, by silica gel chromatography (chloroform/methanol=50:1).

NMR (CDCl₃), δ:
3.47 (2H, ABq), 3.79 (3H, s), 3.81 (3H, s), 3.96 (3H, s), 4.43 (2H, ABq), 5.00 (1H, d), 5.05 (2H, s), 5.18 (2H, ABq), 5.20 (2H, s), 5.87 (1H, q), 6.40 (1H, s), 6.80 (5H, m), 7.15 (1H, s), 7.30 (20H, m)

(d) To a solution of 300 mg of the chloromethyl derivative obtained above in 0.5 ml dimethyl sulfoxide, was added 45 mg of sodium salt of 5-mercapto-1,2,3-thiadiazole, and the mixture was held at room temperature for one hour. Dichloromethane (50 ml) was added to the reaction mixture, and the resulting solution was washed twice with 20 ml of 15% aqueous solution of sodium chloride, dried over anhydrous magnesium sulfate, and concentrated to dryness under reduced pressure. The residue was dissolved in 0.54 ml anisole, 1.54 ml trifluoroacetic acid was added to this solution under ice cooling, and the mixture was held at that temperature for one hour.

Isopropyl ether (10 ml) was added to the reaction mixture, and the precipitate which separated out was collected by filtration, washed with isopropyl ether and dried. This precipitate (185 mg) was suspended in water, and saturated aqueous solution of sodium bicarbonate was added to put the suspension into solution (pH: 7.5). The resulting solution was purified by HP-20 column chromatography (eluent: 5–10% aqueous acetone), giving 75 mg of (6R,7R)-7-[(Z)-2-(2-aminothiazol-4-yl)-2-(1-methoxy-5-hydroxy-4-pyridon-2-yl)methoxyiminoacetamido]-3-(1,2,3-thiadiazol-5-yl)thiomethyl-ceph-3-em-4-carboxylic acid as sodium salt.

NMR (D₂O), δ:
3.48 (2H, ABq), 4.15 (2H, ABq), 4.17 (3H, s), 5.12 (1H, d), 5.33 (2H, s), 5.72 (1H, d), 6.69 (1H, s), 7.10 (1H, s), 7.95 (1H, s), 8.72 (1H, s)

Compounds of Examples 2 through 6 were prepared in much the same manner as in Example 1, except that each of the corresponding reagents [A] was used in place of 5-mercapto 1,2,3-thiadiazole in step (d).

EXAMPLE 2

(6R,7R)-7-[(Z)-2-(2-aminothiazol-4-yl)-2-(1-methoxy-5-hydroxy-4-pyridon-2-yl)methoxyiminoacetamido]-3-[1-(2-hydroxyethyl-1H-tetrazol-5-yl)thiomethyl-ceph-3-em-4-carboxylic acid

[A] 5-Mercapto-1-(2-hydroxyethyl)-1H-tetrazole

NMR (D₂O), δ:
3.50 (2H, ABq), 4.03 (2H, m), 4.13 (3H, s), 4.21 (2H, ABq), 4.54 (2H, m), 5.11 (1H, d), 5.30 (2H, bs), 5.73 (1H, d), 6.66 (1H, s), 7.05 (1H, s), 7.96 (1H, s)

EXAMPLE 3

(6R,7R)-7-[(Z)-2-(2-aminothiazol-4-yl)-2-(1-methoxy-5-hydroxy-4-pyridon-2-yl)methoxyiminoacetamido]-3-(2-methyl-1,3,4-thiadiazol-5-yl)thiomethyl-ceph-3-em-4-carboxylic acid

[A] 5-Mercapto-2-methyl-1,3,4-thiadiazole

NMR (D$_2$O), δ:
2.73 (3H, s), 3.52 (2H, ABq), 4.14 (3H, s), 4.21 (2H, ADq), 5.11 (1H, d), 5.30 (2H, s), 5.72 (1H, d), 6.65 (1H, s), 7.06 (1H, s), 7.85 (1H, s)

EXAMPLE 4

(6R,7R)-7-[(Z)-2-(2-aminothiazol-4-yl)-2-(1-methoxy-5-hydroxy-4-pyridon-2-yl)methoxyiminoacetamido]-3-(1-carboxymethylpyridinium-4-yl)thiomethyl-ceph-3-em-4-carboxylic acid

[A] 1-Carboxymethyl-4-thiopyridone

NMR (D$_2$O), δ:
3.51 (2H, ABq), 4.17 (3H, s), 4.33 (2H, ABq), 5.08 (2H, s), 5.17 (1H, d), 5.34 (2H, s), 5.78 (1H, d), 6.71 (1H, s), 7.10 (1H, s), 7.85 (2H, d), 8.02 (1H, s), 8.41 (2H, d)

EXAMPLE 5

(6R,7R)-7-[(Z)-2-(2-aminothiazol-4-yl)-2-(1-methoxy-5-hydroxy-4-pyridon-2-yl)methoxyiminoacetamido]-3-(1-carboxymethyl-1H-tetrazol-5-yl)thiomethyl-ceph-3-em-4-carboxylic acid

[A] 5-Mercapto-1-carboxymethyl-1H-tetrazole

NMR (D$_2$O), δ:
3.59 (2H, ABq), 4.23 (3H, s), 4.31 (2H, ABq), 5.14 (2H, s), 5.22 (1H, d), 5.39 (2H, ABq), 5.82 (1H, d), 6.76 (1H, s), 7.17 (1H, s), 8.07 (1H, s)

EXAMPLE 6

(6R,7R)-7-[(Z)-2-(2-aminothiazol-4-yl)-2-(1-methoxy-5-hydroxy-4-pyridon-2-yl)methoxyiminoacetamido]-3-(3,4-dihydro-4-methyl-1,1,3-trioxo-2H-1,2,4,6-thiatriazin-5-yl)thiomethyl-ceph-3-em-4-carboxylic acid

[A] 3,4,5,6-Tetrahydro-4-methyl-1,1,3-trioxo-2H-1,2,4,6-thiatriazin-5-thione

NMR (D$_2$O), δ:
3.56 (2H, ABq), 3.41 (3H, s), 4.14 (2H, ABq), 4.18 (3H, s), 5.19 (1H, d), 5.29 (2H, s), 5.79 (1H, d), 6.70 (1H, s), 7.11 (1H, s), 8.00 (1H, s)

EXAMPLE 7

(6R,7R)-7-[(Z)-2-(2-aminothiazol-4-yl)-2-(1-methoxy-5-hydroxy-4-pyridon-2-yl)methoxyiminoacetamido]-3-acetoxymethyl-ceph-3-em-4-carboxylic acid (a) To a solution of 700 mg (Z)-2-(2-tritylaminothiazol-4-yl)-2-(1-methoxy-5-p-methoxybenzyloxy-4-pyridon-2-yl)methoxyiminoacetic acid and 440 mg benzhydryl 7-aminocophalosporanate in 20 ml dichloromethane, were added at −10° to −15° C. 0.4 ml pyridine and 0.1 ml phosphorus oxychloride, and the mixture was held at that temperature for 30 minutes. Dichloromethane (50 ml) and 15% aqueous solution of sodium chloride (30 ml) were added to the reaction mixture, and the organic layer was washed twice with 20 ml of 15% aqueous solution of sodium chloride, dried over anhydrous magnesium sulfate, and concentrated to dryness. The residue was purified by silica gel column chromatography (chloroform/methanol=50:1), giving 500 mg of benzhydryl (6R,7R)-7-[(Z)-2-(2-tritylaminothiazol-4-yl)-2-(1-methoxy-5-p-methoxybenzyloxy-4-pyridon-2-yl)methoxyiminoacetamido]-3-acetoxymethyl-ceph-3-em-4-carboxylate.

NMR (CDCl$_3$), δ:
2.00 (3H, s), 3.40 (2H, ABq), 3.77 (3H, s), 3.95 (3H, s), 4.70 (1H, d), 4.95–5.20 (6H, m), 5.90 (1H, q), 6.41 (1H, s), 6.84 (2H, d), 6.88 (1H, s), 6.93 (1H, s), 7.13 (1H, s), 7.25–7.45 (28H, m)

(b) The benzhydryl ester obtained above was dissolved in 1 ml anisole, 2.8 ml trifluoroacetic acid was added to this solution under ice cooling, and the mixture was held under the same condition for one hour. Isopropyl ether (15 ml) was added to the reaction mixture, and the precipitate which separated out was collected by filtration, washed with isopropyl ether and dried. It was then suspended in water, saturated aqueous solution of sodium bicarbonate was added to put the suspension into solution (pH: 7.5), and the resulting solution was purified by HP-20 column chromatography (eluent: 10% aqueous acetone), giving 180 mg of (6R, 7R)-7-[(Z)-2-(2-aminothiazol-4-yl)-2-(1-methoxy-5-hydroxy-4-pyridon-2-yl)methoxyiminoacetamido]-3-acetoxymethyl-ceph-3-em-4-carboxylic acid as sodium salt.

NMR (D$_2$O), δ:
2.14 (3H, s), 3.45 (2H, ABq), 4.16 (3H, s), 4.86 (2H, ABq), 5.18 (1H, d), 5.34 (2H, s), 5.81 (1H, d), 6.71 (1H, s), 7.10 (1H, s), 8.02 (1H, s)

EXAMPLE 8

6R,7R)-7-[(Z)-2-(2-aminothiazol-4-yl)-2-(1-methoxy-5-hydroxy-4-pyridon-2-yl)methoxyiminoacetamido]-3-(2,5-dihydro-2-methyl-5-oxo-6-hydroxy-1,2,4-triazin-3-yl)thiomethyl-ceph-3-em-4-carboxylic acid The chloromethyl derivative obtained in step (d) of Example 1 (120 mg) was dissolved in 0.26 ml anisole, 0.74 ml trifluoroacetic acid was added to this solution under ice cooling, and stirring was continued for one hour. Isopropyl ether was added to the reaction mixture, and the precipitate which separated out was collected by filtration and dried.

It was dissolved in 1 ml dimethyl sulfoxide, 36 mg sodium iodide and 33 mg sodium salt of 3-mercapto-2,5-dihydro-2-methyl-5-oxo-6-hydroxy-1,2,4-triazine were added to this solution, and the resulting mixture was held at room temperature for one hour. Ethyl acetate was added to the reaction mixture, and the precipitate which separated out was collected by filtration, washed with acetone, dried, and purified by HP-20 column chromatography (eluent: water to 5% aqueous acetone), giving 37 mg of (6R,7R)-7-[(Z)-2-(2-aminothiazol-4-yl) -2-(1-methoxy-5-hydroxy-4-pyridon-2-yl) -methoxyiminoacetamido]-3-(2,5-dihydro-2-methyl-5-oxo-6-hydroxy-1,2,4-triazin-3-yl)thiomethyl-ceph-3-em-4-carboxylic acid as sodium salt.

NMR (D$_2$O), δ:

3.57 (2H, ABq), 3.74 (3H, s), 4.22 (3H, s), 4.28 (2H, ABq), 5.22 (1H, d), 5.38 (2H, s), 5.82 (1H, s), 6.74 (1H, s), 7.16 (1H, s), 8.03 (1H, s)

EXAMPLE 9

6R,7R)-7-[(Z)-2-(2-aminothiazol-4-yl)-2-(1-ethoxy-5-hydroxy-4-pyridon-2-yl)methoxyiminoacetamido]-3-(1,2,3-thiadiazol-5-yl)thiomethyl-ceph-3-em-4-carboxylic acid (a) (Z)-2-(2-tritylaminothiazol-4-yl)-2-(1-ethoxy-5-p-methoxybenzyloxy-4-pyridon-2-yl)methoxyiminoacetic acid (1.65 g) was obtained from 1.15 g 1-ethoxy-5-p-methoxybenzyloxy-2-hydroxymethyl-4-pyridone in much the same manner as in steps (a) and (b) of Example 1.

NMR (CDCl₃), δ:
1.28 (3H, t), 3.78 (3H, s), 4.21 (2H, q), 5.00 (2H, s), 5.16 (2H, s), 6.64 (1H, s), 6.85 (2H, d), 6.87 (1H, s), 7.2–7.35 (19H, m)

(b) The product obtained above (180 mg) was dissolved in 5 ml dichloromethane, 115 mg p-methoxybenzyl (6R,7R) -7-amino-3-(1,2,3-thiadiazol-5-yl)thiomethyl-ceph-3-em-4-carboxylate was added to this solution, and the resulting mixture was cooled to −10° to −15° C. Pyridine (0.1 ml) and phosphorus oxychloride (25 ml) were then added, and the mixture was held at that temperature for one hour. Dichloromethane (30 ml) was added to the reaction mixture, and the resulting solution was washed twice with 10 ml of 15% aqueous solution of sodium chloride, dried over anhydrous magnesium sulfate, and concentrated to dryness under reduced pressure.

The residue was purified by silica gel column chromatography (chloroform/methanol=50:1), giving 120 mg of p-methoxybenzyl (6R,7R)-7-[(Z)-2-(2-tritylaminothiazol-4-yl)-2-(1-ethoxy-5-p -methoxybenzyloxy-4-pyridon-2-yl)methoxyiminoacetamido]-3-(1,2,3-thiadiazol-5-yl)thiomethyl-ceph-3-em-4-carboxylate.

NMR (CDCl₃), δ:
1.27 (3H, t), 3.44 (2H, ABq), 3.78 (3H, s), 3.80 (3H, s), 4.12 (2H, ABq), 4.15 (2H, q), 4.95 (1H, d), 5.05 (2H, s), 5.11 (2H, ABq), 5.16 (2H, s), 5.81 (1H, q), 6.48 (1H, s), 6.82 (1H, s), 6.87 (4H, d), 7.05 (1H, s), 7.16 (1H, s), 7.30 (20H, m), 8.41 (1H, s)

(c) The product obtained above (120 mg) was dissolved in 0.23 ml anisole, 0.65 ml trifluoroacetic acid was added under ice cooling, and the mixture was held at that temperature for one hour. Isopropyl ether (4 ml) was added to the reaction mixture, and the precipitate which separated out was collected by filtration.

It was suspended in water, saturated aqueous solution of sodium bicarbonate was added to put the suspension into solution (pH: 7.5), and the resulting solution was purified by Hp-20 column chromatography (eluent: 10% aqueousacetone), giving 50 mg of (6R,7R) -7-[(Z)-2-(2-aminothiazol-4-yl)-2-(1-ethoxy-5-hydroxy-4-pyridon-2-yl)methoxyiminoacetamido]-3-(1,2,3-thiadiazol -5-yl)thiomethyl-ceph-3-em-4-carboxylic acid as sodium salt.

NMR (D₂O), δ:
1.38 (3H, t), 3.49 (2H, ABq), 4.14 (2H, ABq), 4.42 (2H, q), 5.13 (1H, d), 5.32 (2H, ABq), 5.74 (1H, d), 6.71 (1H, s), 7.09 (1H, s), 7.97 (1H, s), 8.73 (1H, s)

What is claimed is:

1. Cephalosporin compounds represented by the following formula:

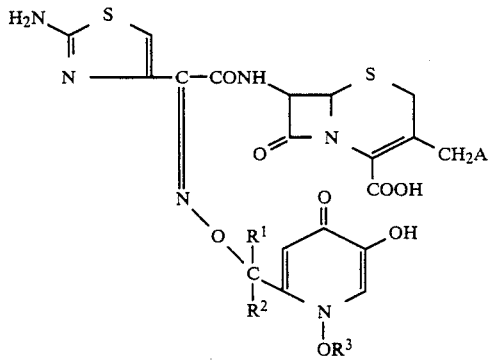

wherein $R^1$ and $R^2$ are the same or different and represent a hydrogen atom or a lower alkyl group of 1 to 5 carbon atoms; $R^3$ is a lower alkyl group which may optionally be substituted with at least one halogen atom, an alkenyl group, or a cycloalkylmethyl group of 3 to 6 carbon atoms; and A is a hydrogen atom or an acetoxy or a 5- or 6-membered heterocyclicthio group of a formula (I-1):

—S—Het      (I-1)

wherein Het is a heteroring selected from pyridyl, thiazolyl, tetrazolyl, triazolyl, triazinyl, and thiatriazinyl, and pharmacologically acceptable salts thereof.

2. A cephalosporin compound according to claim 1 which is (6R,7R)-7-[(Z)-2-(2-aminothiazol-4-yl)-2-(1-methoxy-5-hydroxy -4-pyridon-2-yl)methoxyiminoacetamido]-3-(1,2,3-thiadiazol-5-yl) thiomethyl-ceph-3-em-4-carboxylic acid.

3. A cephalosporin compound according to claim 1 which is (6R,7R)-7-[(Z)-2-(aminothiazol-4-yl)-2-(1-methoxy-5-hydroxy 4pyridon-2-yl)methoxyiminoacetamido]-3-[1-(2-hydroxyethyl)-1H -tetrazol-5-yl)thiomethyl-ceph-3-em-4-carboxylic acid.

4. A cephalosporin compound according to claim 1 which is (6R,7R)-7-[(Z)-2-(2-aminothiazol-4-yl)-2-(1-methoxy-5-hydroxy -4-pyridon-2-yl)methoxyiminoacetamido]-3-(2-methyl-1,3,4-thiadiazol -5-yl)thiomethyl-ceph-3-em-4-carboxylic acid.

5. A cephalosporin compound according to claim 1 which is (6R,7R)-7-[(Z)-2-(2-aminothiazol-4-yl)-2-(1-methoxy-5-hydroxy -4-pyridon-2-yl)methoxyiminoacetamido]-3-(1-carboxymethylpyridinium -4-yl)thiomethyl-ceph-3-em-4-carboxylic acid.

6. A cephalosporin compound according to claim 1 which is (6R,7R)-7-[(Z)-2-(2-aminothiazol-4-yl)-2-(1-methoxy-5-hydroxy -4-pyridon-2-yl)methoxyiminoacetamido]-3-(1-carboxymethyl-1H -tetrazol-5-yl)thiomethyl-ceph-3-em-4-carboxylic acid.

7. A cephalosporin compound according to claim 1 which is (6R,7R)-7-[(Z)-2-(2-aminothiazol-4-yl)-2-(1-methoxy-5-hydroxy -4-pyridon-2-yl)methoxyiminoacetamido]-3-(3,4-dihydro-4-methyl-1,1,3-trioxo-2H-1,2,4,6-thiatriazin-5-yl)thiomethyl-ceph-3-em-4-carboxylic acid.

8. A cephalosporin compound according to claim 1 which is (6R,7R)-7-[(Z)-2-(2-aminothiazol-4-yl)-2-(1-methoxy-5-hydroxy-4-pyridon-2-yl)methoxyiminoacetamido]-3-acetoxymethyl-ceph-3-em-4-carboxylic acid.

9. A cephalosporin compound according to claim 1 which is (6R,7R)-7-[(Z)-2-(2-aminothiazol-4-yl)-2-(1-methoxy-5-hydroxy-4-pyridon-2-yl)methoxyiminoacetamido]-3-(2,5-dihydro-2-methyl-5-oxo-6-hydroxy-1,2,4-triazin-3-yl)thiomethyl-ceph-3-em-4-carboxylic acid.

10. A cephalosporin compound according to claim 1 which is (6R,7R)-7-[(Z)-2-(2-aminothiazol-4-yl)-2-(1-methoxy-5-hydroxy-4-pyridon-2-yl)methoxyiminoacetamido]-3-(1,2,3-thiadiazol-5-yl) thiomethyl-ceph-3-em-4-carboxylic acid.

11. An antibacterial pharmaceutical composition containing an effective amount of a compound of claim 1 and a pharmaceutically acceptable carrier.

12. Cephalosporin compounds according to claim 1, wherein said heteroring contains a substituent group selected from the group consisting of hydroxy alkyl, alkyl, carboxyalkyl, oxo and hydroxy.

* * * * *